United States Patent [19]

Campbell et al.

[11] Patent Number: 4,861,380
[45] Date of Patent: Aug. 29, 1989

[54] COMPOSITION

[75] Inventors: Frederick Campbell, Manchester; John M. Geary, Heywood; John D. Schofield, Bury, all of England

[73] Assignee: Imperial Chemical Industries PLC, London, England

[21] Appl. No.: 263,985

[22] Filed: Oct. 22, 1988

Related U.S. Application Data

[63] Continuation of Ser. No. 83,878, Aug. 10, 1987, abandoned, which is a continuation of Ser. No. 813,776, Dec. 27, 1985, abandoned.

[30] Foreign Application Priority Data

Jan. 22, 1985 [GB] United Kingdom ................. 8501527
Jun. 17, 1985 [GB] United Kingdom ................. 8515327

[51] Int. Cl.$^4$ ............................................. C04B 14/00
[52] U.S. Cl. ..................................... 106/504; 106/499
[58] Field of Search .......... 106/308 N, 308 C, 308 M, 106/504, 499

[56] References Cited

U.S. PATENT DOCUMENTS 3,882,088  7/1975  Thompson .
4,153,754  5/1979  Huisman .
4,224,212  9/1980  Tophau .
4,398,355  8/1983  Stansfield .
4,398,955  8/1983  Stansfield et al. .............. 106/308 N
4,415,705  11/1983 Hutter .............................. 525/167.5
4,518,435  5/1985  Stansfield .

FOREIGN PATENT DOCUMENTS 0446054  4/1942  Belgium .
2001083  1/1979  United Kingdom .

OTHER PUBLICATIONS

Chemistry of Organic Compounds, by Noller, p. 696.

Primary Examiner—Joseph L. Schofer
Assistant Examiner—N. Sarofim
Attorney, Agent, or Firm—Cushman, Darby & Cushman

[57] ABSTRACT

A composition comprising a finely-divided non-magnetic solid and a dispersant comprising a poly($C_{2-4}$-alkyleneimine) carrying at least two mono- or poly-(carbonyl-$C_{1-7}$-alkyleneoxy) groups, a dispersion of the composition in an organic medium and a dispersant comprising a poly($C_{2-4}$-alkyleneimine) carrying at least two carbonyl-$C_{1-7}$-alkyleneoxy groups.

11 Claims, No Drawings

COMPOSITION

This is a continuation of application Ser. No. 083,878, filed Aug. 10, 1987, which is a continuation of application Ser. No. 813,7756, which was filed Dec. 27, 1985 both now abandoned.

This specification describes an invention relating to a novel dispersible composition of finely divided non-magnetic solid and a dispersant and to a dispersion of the composition in an organic medium.

The Composition

According to the present invention there is provided a composition comprising a finely-divided non-magnetic solid and a dispersant comprising a poly($C_{2-4}$-alkyleneimine) carrying at least two mono- or poly-(carbonyl-$C_{1-7}$-alkyleneoxy) groups.

The composition may comprise an intimate mixture of the two components but preferably comprises a coating of the surfactant on finely divided primary particles of the solid which preferably have a mean diameter below 10 microns and more preferably below 5 microns. The composition may be dry, in which case the primary particles of the solid may be aggregated, or it may be in the form of a dispersion of the solid in an organic medium, preferably one which is a liquid, or is at least plastic, under ambient or processing conditions.

The composition preferably contains from 1% to 100%, and more preferably from 1% to 30%, by weight of the dispersant, based on the weight of the solid. In the dispersion form, the composition preferably contains from 5% to 95% by weight of the solid, the precise quantity depending on the nature of the solid and the relative densities of the solid and liquid. For example, a dispersion in which the solid is an organic material, such as an organic pigment, preferably contains from 15% to 60% by weight of the solid, whereas a dispersion in which the solid is an inorganic material, such as an inorganic pigment, filler or extender, preferably contains from 40% to 90% of the solid, based on the total weight of the composition.

The composition may be prepared by mixing the components or the dispersant may be added to the solid during the preparation of the latter, preferably during the later or finishing stages of preparation. The composition may also be prepared by subjecting a mixture of the solid, the surfactant, preferably in the organic medium, to a grinding operation sufficient to reduce the particle size of the solid to below 10 microns. Where the organic medium is a volatile liquid this may be subsequently removed by evaporation, if the composition is required in a dry form. Where the organic medium is a solid or plastic material at ambient temperatures, e.g. a polar resin, the mixing of the components and subsequent grinding operation may be carried out at an elevated temperature so that the organic medium and the composition is in a fluid or plastic, form.

The composition, whether dry or in the form of a dispersion, may contain other ingredients, such as resins (where these do not already constitute the organic medium), binders, fluidising agents, anti-sedimentation agents, plasticisers, levelling agents and preservatives. The present composition is compatible with the fluidising agents disclosed in UK Patent Specifications Nos.1508576 and 2108143. The fluidising agent described in UK 1508576 is a substituted ammonium salt of a coloured acid wherein there are from 19 to 60 carbon atoms in at least 3 chains attached to the N atom of the substituted ammonium ion. The fluidising agent described in UK 2108143 is a water-insoluble disazo compound comprising a central divalent group free from acidic and other ionic substituents linked, through azo groups, to two monovalent end groups, one end group being free from acidic and other ionic substituents and the other carrying a single substituted ammonium salt group. Such fluidising agents are useful for enhancing the fluidity of the dispersion form of the present compositions and especially where the organic medium is an ester, a ketone or an aromatic solvent, such as xylene or chlorobenzene.

The composition is particularly suitable for use in paints, especially high solids paints, inks, especially flexographic, gravure and screen inks, and non-aqueous ceramic processes, especially tape-coating, doctor-blade, extrusion and injection moulding type processes. Paint systems in which the composition is particularly suitable include those based on alkyd resins, particularly medium- and short-oil alkyd resins, oil-free polyester resins, polyol resins, urethane resins and acrylic resins. Particularly suitable hardeners or crosslinkers include melamine-formaldehyde resins, particularly butylated melamine- formaldehyde and hexamethoxymethyl-melamine resins, urea- formaldehyde resins, urethanes and isocyanates. Gravure inks in which the composition is particularly suitable include gravure inks of types C, D and E as classified by the Gravure Technical Association of New York.

The Solid

The solid may be any non-magnetic material, especially a material which it is desired to stabilise in a finely divided state in an organic medium. Examples of suitable solids are pigments for solvent inks; pigments, extenders and fillers for paints and plastics materials; dyes, especially disperse dyes; optical brightening agents and textile auxiliaries for solvent dyebaths, inks and other solvent application systems; solids for oil-based and invert-emulsion drilling muds; dirt and soil particles in dry cleaning fluids; particulate ceramic materials; and biocides, agrochemicals and pharmaceuticals which are applied as dispersions in organic media.

A preferred solid is a pigment from any of the recognized classes of pigments described, for example, in the Third Edition of the Colours Index (1971) and subsequent revisions of, and supplements thereto, under the chapter headed "Pigments".

Examples of inorganic pigments are titanium dioxide, zinc oxide, Prussian blue, cadmium sulphide, iron oxides, vermillion, ultramarine and the chrome pigments, including chromates, molybdates and mixed chromates and sulphates of lead, zinc, barium, calcium, and mixtures and modifications thereof which are commercially available as greenish-yellow to red pigments under the names primrose, lemon, middle, orange, scarlet and red chromes.

Examples of organic pigments are those from the azo, disazo, condensed azo, thioindigo, indanthrone, isoindanthrone, anthanthrone, anthraquinone, isodibenzanthrone, triphendioxazine, quinacridone and phthalocyanine series, especially copper phthalocyanine and its nuclear halogenated derivatives, and also lakes of acid, basic and mordant dyes. Carbon black, although strictly inorganic, behaves more like an organic pigment in its dispersing properties. Preferred organic pigments are phthalocyanines, especially copper phthalocyanines, monoazos, disazos, indanthrones, anthranthrones, quinacridones and carbon blacks.

Examples of extenders and fillers are talc, kaolin, silica, barytes and chalk.

Examples of suitable particulate ceramic materials are alumina, silica, zirconia, titania, silicon nitride, boron nitride, silicon carbide, boron carbide, mixed silicon-aluminium nitrides and metal titanates Examples of agrochemicals include the fungicides flutriafen, carbendazim, chlorothalonil and mancozeb.

The Organic Medium

Where the composition of the present invention is in the form of a dispersion, the organic medium is preferably a polar organic medium or a substantially non-polar aromatic hydrocarbon or halogenated hydrocarbon. By the term "polar" in relation to the organic medium is meant an organic liquid or resin capable of forming moderate to strong bonds as described in the article entitled "A Three Dimensional Approach to Solubility" by Crowley et al in Journal of Paint Technology, Vol.38, 1966, at page 269. Such organic media generally have a hydrogen bonding number of 5 or more as defined in the above-mentioned article.

Examples of suitable polar organic liquids are amines, ethers, especially lower alkyl ethers, organic acids, esters, ketones, glycols, alcohols and amides. Numerous specific examples of such moderately and strongly hydrogen bonding liquids are given in the book entitled "Compatibility and Solubility" by Ibert Mellan (published in 1968 by Noyes Development Corporation) in Table 2.14 on pages 39 and 40 and these liquids all fall within the scope of the term polar organic liquid as used in this specification.

Preferred polar organic liquids are dialkyl ketones, alkyl esters of alkane carboxylic acids and alkanols, especially such liquids containing up to, and including, a total of 6 carbon atoms. As examples of the preferred and especially preferred liquids there may be mentioned dialkyl and cycloalkyl ketones, such as acetone, methyl-ethyl-ketone, di-ethylketone, di-iso-propylketone, methyliso-butyl-ketone, di-iso-butylketone, methyl-iso-amyl-ketone, methyl-n-amyl-ketone and cyclohexanone; alkyl esters such as methyl acetate, ethyl acetate, isopropyl acetate, butyl acetate, ethyl formate, methyl propionate and ethyl butyrate, glycols and glycol esters and ethers, such as ethylene glycol, 2-ethoxyethanol, 3-methoxypropylpropanol, 3-ethoxypropylpropanol, 2-butoxyethyl acetate, 3-methoxypropyl acetate, 3-ethoxypropyl acetate and 2-ethoxyethyl acetate, alkanols such as methanol, ethanol, n-propanol, isopropanol, n-butanol and isobutanol and dialkyl and cyclic ethers such as diethylether and tetrahydrofuran.

The substantially non-polar, organic liquids which may be used, either alone or in admixtrue with the aforementioned polar solvents, are aromatic hydrocarbons, such as toluene and xylene, and halogenated aliphatic and aromatic hydrocarbons, such as trichloroethylene, perchloroethylene and chlorobenzene. However, aliphatic hydrocarbons, such as petroleum fraction and white spirit are preferably only employed in admixtrue with the above-mentioned polar solvents and the proportion of an aliphatic hydrocarbon should preferably not exceed a level which reduces the ability of the mixture to completely dissolve the resins which may form a part of the dispersion because the are required in end use formulations, such as inks, paints and ceramic moulding compositions.

Examples of suitable polar resins, as the medium for the dispersion form of the present invention, are film-forming resins such as are suitable for the preparation of inks, paints and chips for use in various applications such as paints and inks. Specific examples of such polar resins are polyesters, such as polyethylene terephthalate, nitrocellulose, cellulose acetate and propionate and polacrylates, polyamides, such as Versamid (Trade Mark) and Wolfamid (Trade Mark), and celluolose ethers, such as ethyl-cellulose and ethyl-hydroxyethyl-cellulose.

The Dispersant

Each alkylene group in the carbonyl-$C_{1-7}$-alkyleneoxy group (hereinafter referred to as the "CAO group") or the poly(carbonyl$C_{1-7}$-alkyleneoxy) group (hereinafter referred to as the "PCAO chain") preferably contains from 3 to 6 carbon atoms, an especially preferred alkylene group being pentamethylene wherein the CAO group is 5-oxypentamethylene-1-carbonyl (hereinafter referred to as "OPMC") which is derivable from E-caprolactone. The PCAO chain may contain a mixture of alkylene groups of different length but is preferably a homopolymer, especially of OPMC. THe PCAO chain or the CAO group may carry a chain-stopping terminal group at the free end, such as optionally substituted alkyl, e.g. alkyl, alkoxyalkyl or haloalkyl, where the absence of a terminal hydroxy group prevents formation or further growth of the PCAO chain. The PCAO chain preferably contains from 2 to 100, and more preferably from 3 to 80, CAO groups.

The CAO group and PCAO chain can be conveniently represented by the general formula:

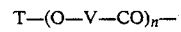        I wherein

T is H or a terminal chain stopping group;

V is a $C_{1-7}$-alkylene group;

and n is a number from 1 to 100.

When n =1 Formula I represents a CAO group and when n>1 Formula I represents a PCAO chain.

Each CAO group or PCAO chain is preferably linked to the poly($C_{2-4}$-alkyleneimine) (hereinafter referred to as "PAI") through a covalent "amide" link,

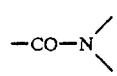        I formed between a terminal carbonyl group (—CO—) of the CAO group or PCAO chain and the nitrogen atom (N) of a primary or secondary amino group in the PAI, or through an ionic "salt" link,

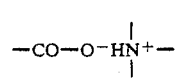        III between a terminal carboxylate group (—CO—O$^-$) of the CAO group or the PCAO chain and the positively charged nitrogen atom (+N) of a substituted ammonium group in the PAI. Because the dispersant contains at least two CAO groups or PCAO chains it may contain a mixture of amide and salt links depending upon the severity of the conditions under which it is prepared.

The dispersant can be conveniently represented by the following general formula:

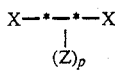    IV wherein X—*—*—X represents a poly($C_{2-4}$-alkylene)imine (PAI);

Z represents a CAO group or PCAO chain linked to the PAI through an amide or salt link;

and p is a number from 2 to 2000.

The dispersant preferably contains from 4 to 2000 (p=4 to 2000) and more preferably from 4 to 1000 (p=4 to 1000) CAO groups or PCAO chains.

The PAI is preferably a poly(ethyleneimine), hereinafter referred to as "PEI", which may be branched or straight-chained. A preferred dispersant comprises PEI carrying at least two CAO groups or PCAO chains attached thereto by amide and/or salt links. The PAI preferably has a weight-average molecular weight from 500 to 600,000 and more preferably from 1,000 to 200,000.

The dispersant may be derived from a PAI and a CAO acid or a PCAO acid, i.e. a compound of the formula:

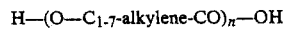    V in which n is from 1 to 100, or a cyclic precursor thereof, such as a lactone. The length of the PCAO chain in the PCAO acid may be controlled by the presence of chain stopper, such a carboxylic acid free from hydroxy groups, in the preparative process. Where the dispersant carries PCAO chains formed by the polymerisation of a carbonylalkyleneoxy monomer, such as a lactone, in the presence of the PAI, there is less need for a chain stopper, because the PCAO chain grow on the PAI and cannot react together; in such a case the pendant PCAO chains may be terminated by hydroxy groups.

The dispersant may be derived from a PAI having at least two primary, secondary or tertiary amino groups, and a CAO or PCAO acid, in which case reaction between a p-, s- or t-amino group in the PAI and a terminal carboxyl group on the CAO or PCAO acid forms an amide or salt link. If the PAI contains a t-amino group only salt links can be formed, otherwise salt and/or amide links are formed depending on the reaction conditions. Generally, mild reaction conditions such as low temperatures and/or short reaction times promote the formation of salt links and more severe conditions, such as high temperatures and/or long reaction times promote the formation of amide links in a manner which is familiar to the skilled chemist.

The dispersant comprising a PAI chain carrying CAO groups is novel and forms feature of the invention. Each CAO group is preferably terminated by a group which is free form OH/NH$_2$ groups, such as alkylcarbonyl. Termination is conveniently effected by reaction of a CAO acid, or lactone precursor, with a carboxylic acid which is free from hydroxy or amino groups, e.g. an alkane- or an alkoxyalkane-carboxylic acid, such as caproic acid, lauric acid, stearic acid, methoxyacetic acid and especially by a such an acid containing twelve or more, preferably 12 to 25, carbon atoms.

Where the dispersant contains free amino groups these may be converted into substituted ammonium groups by reaction with an acid or a quaternising agent so that the dispersant is in the form of a substituted ammonium salt. Suitable reagents for this purpose are mineral and strong organic acids or acidic salts, such as acetic acid, sulphuric acid, hydrochloric acid, alkylsulphonic acids, alkyl hydrogen sulphates and arylsulphonic acids, especially acid forms of dyes and pigments, and quaternising agents such as dimethyl sulphate (DMS), methyl and ethyl halides and diethyl sulphate (DES).

Where the solid is an inorganic material, such as an inorganic pigment, extender or filler, it is preferred that the dispersant is in the form of the free amine or a salt with a mineral acid or a quaternary ammonium salt. Where the solid is an organic material, such as an organic pigment or dye, it is often preferred that the dispersant is in the form of a substituted ammonium salt between free amine groups in the PAI portion of the dispersant and an aromatic acid containing from 2 to 10 benzene rings, more especially a coloured acid. Such salts are especially effective dispersants where the organic medium is an alcohol, such as ethanol or isopropanol. By the term coloured acid is meant an organic pigment or dye containing at least one, preferably from 1 to 6, acid groups, especially sulphonic, phosphonic or carboxylic acid groups. It is convenient to use an acid form of the organic pigment which forms the solid in the compositions. Thus, a preferred coloured acid for the preparation of a composition in which the solid is a copper phthalocyanine or a similarly deeply coloured pigment, is a copper phthalocyanine sulphonic acid, especially such an acid containing, on average, from 0.5 to 3 sulphonic acids groups per molecule, The dispersant may be prepared by reaction of a PAI with a PCAO acid or precursor thereof, such as a $C_{1-7}$-alkylenelactone or hydroxy-$C_{1-7}$-alkylenecarboxylic acid at a temperature from 25° C. to 250° C. for up to 24 hours. Under mild conditions (low temperature and/or short reaction time) salt links are formed and under more severe conditions (higher temperature and/or longer reaction time) amide, or a mixture of amide and salt links are formed.

The CAO or PCAO acid may be prepared by heating a hydroxycarboxylic acid or lactone with a carboxylic acid which is free from hydroxy groups, such as acetic acid, caproic acid, lauric acid and methoxyacetic acid. The absence or degree of polymerisation is controlled by the relative proportions of the mono and bifunctional reactants. Reaction is conveniently performed at a temperature from 100° C. to 250° C., preferably from 130° C. to 200° C., in the presence of an esterification catalyst, such as tetrabutyl titanate, zirconium naphthenate, zinc acetate or toluenesulphonic acid.

Where the PAI is PEI, the weight ratio of CAO acid or PCAO acid to PEI is preferably at least 1:1 and is more preferably in the range from 1:1 to 30:1. It is especially preferred, in the case of a dispersant based on PEI and a PCAO acid derived from E-caprolactone, that the weight ratio of the PCAO acid to PEI is from 1.5:1 to 30:1. The equivalent molar ratios of the two reactants depends, of course, on their respective average molecular weights. It has been found that a dispersant in which the PCAO chain is fairly short, i.e. containing from 2 to 7 CAO groups (mol wt =400 to 1000) and the weight ratio of PCAO to PEI is fairly low, i.e. from 1.5:1 to 3:1, is particularly suitable for use in a dispersion of the solid in an alkanol. It has also been found possible to design a dispersant which is particularly suitable for use in a dispersion of the solid in an ester or a ketone by using a similar PCAO chain (i.e. containing 2 to 7 CAO groups) and a somewhat higher weight ratio of PCAO to PEI, i.e. from 3:1 to 5:1 or a rather longer PCAO chain containing 7 or more CAO groups (i.e. mol wt =1000 or more) and a much higher weight ratio of PCAO to PEI, e.g. from 5:1 to 20:1.

To minimise degradation of the reactants and products the reactions are preferably performed under an inert atmosphere, such as nitrogen.

The invention is further illustrated by the following examples in which all parts and percentages are by weight unless otherwise indicated.

Intermediate 1

A mixture of 112 g of E-caprolactone, 9.2 g of n-caproic acid and 0.1g of tetrabutyl titanate was stirred under nitrogen for 18 hours at 180° C. to 190° C. The product was a hard wax with an acid value of 36mg KOH/g. It thus contains, on average, 12.6 5-oxypentamethylene-1-carbonyl (OPMC) groups.

Intermediate 2

A mixture of 582 g of E-caprolactone, 32.25 g of methoxyacetic acid and 0.5 g of tetrabutyltitanate was stirred under nitrogen for 20 hours at 170° C. to 180° C. The product was a hard wax with an acid value of 35.2 mg KOH/g. It therefore contains, on average, 13.2 OPMC groups.

Intermediate 3

A mixture of 500 g of E-caprolactone, 73 g of lauric acid and 0.5 g of tetrabutyltitanate was stirred under nitrogen for 20 hours at 170° C. to 180° C. The product was a hard wax with an acid value of 36.35 mg KOH/g. It therefore contains, on average, 11.8 OPMC groups.

Intermediate 4

A mixture of 250 g of E-caprolactone, 88 g of lauric acid and 0.2 g of tetrabutyltitanate was stirred under nitrogen for 8 hours at 160° C. to 180° C. The product was a wax with an acid value of 75.7 mg.KOH/g. It therefore contains, on average, 4.75 OPMC groups.

Intermediate 5

A mixture of 485 g of E-caprolactone, 34 g of lauric acid and 0.1 g of tetrabutyltitanate was stirred under nitrogen for 19 hours at 70° C. to 190° C. The product was a hard wax with an acid value of 18.6 mg.KOH/g. It therefore contains, on average, 24.7 OPMC groups.

Intermediate 6

A mixture of 485 g of E-caprolactone, 22.4 g of lauric acid and 0.1 g of tetrabutyltitanate was stirred under nitrogen for 19 hours at 170° C. to 190° C. The product was a hard wax with an acid value of 12.4 mg.KOH/g. and thus contains, on average, 37.9 OPMC

Intermediate 7

A mixture of 500 g of E-caprolactone, 17 g of lauric acid and 1.0 g of tetrabutyltitanate was stirred under nitrogen for 19 hours at 170° C. to 190° C. The product was a hard wax having an acid value of 9.9 mg KOH/g and thus contains, on average, 47.9 OPMC groups.

Intermediate 8

A mixture o f 460 g of E-caprolactone, 45 g of methoxyacetic acid and 1 g of tetrabutyl titanate was stirred under nitrogen for 8 hours at 160° C. to 180° C. The product was a hard wax with an acid value of 59 mg.KOH/g. It thus contains, on average, 7.5 OPMC groups.

Intermediate 9

A mixture of 450 g of E-caprolactone, 71 g of methoxyacetic acid and 1 g of tetrabutyl titanate was stirred under nitrogen for 8 hours at 160° C. to 180° C. The product was a wax with an acid value of 84 mg.KOH/g. It thus contains, on average, 5.1 OPMC groups.

Intermediate 10

A mixture of 400 g of E-caprolactone, 115 g of methoxyacetic acid and 1 g of tetrabutyl titanate was stirred under nitrogen for 8 hours at 160° C. to 180° C. The product was a wax with an acid value of 147 mg.KOH/g. It thus contains, on average, 2.6 OPMC groups.

Intermediate 11

A mixture of 228 g of E-caprolactone, 200 g of lauric acid and 0.2 g of tetrabutyl titanate was stirred under nitrogen for 10 hours at 160° C. to 180° C. The product was a wax with an acid value of 139.2 mg.KOH/g. It thus contains, on average, 1.8 OPMC groups.

Intermediate 12

A mixture of 159 g of E-caprolactone, 279 g of lauric acid and 0.2 g of tetrabutyl titanate was stirred under nitrogen for 8 hours at 160° C. to 180° C. The product was a wax with an acid value of 193 mg.KOH/g. It therefore contains, on average, 0.8 OPMC groups.

Dispersant 1

A mixture of 32.5 g of Intermediate 1 and 1.25 g of a dry polyethylenimine having a weight-average molecular weight in the region of 100,000, available from BASF under the name "POLYMIN Waterfree" (POLYMIN is a trade mark), was stirred under nitrogen for 8 hours at 120° C. The product was a wax of equivalent 3175.

Dispersant 2

This was prepared in a similar manner to Dispersant 1, but using 40 g of Intermediate 1 and 3.33 g of "POLYMIN Waterfree". The product was a wax of equivalent 1510.

Dispersant 3

This was prepared in a similar manner to Dispersant 1, but using 40 g of Intermediate 1 and 13.3 g of "POLYMIN Waterfree". The product was a sticky wax of equivalent 475.

Dispersant 4

A mixture of 10.8 g of the product of Dispersant 1 and 10.8 g of tetrahydrofuran was stirred and heated until a clear solution was obtained. The solution was cooled to 35° C. and 0.405 g of dimethyl sulphate was added. The mixture was then stirred for a further hour at 65°-70° C. The tetrahydrofuran was then removed from the mixture by distillation.

Dispersant 5

This was prepared in a similar manner to Dispersant 4, but using 10.24 g of the product of Dispersant 2, 10.24 g of tetrahydrofuran and 0.81 g of dimethyl sulphate.

Dispersant 6

A mixture of 16.1 g of the product of Dispersant 3 and 16.1 g of tetrahydrofuran was stirred and heated. A solution was obtained, but it was not completely clear. The solution was cooled to 40° C., and 4.05 g of dimethyl sulphate was added slowly. There was a vigorous exotherm. The mixture was then stirred for a further hour at 65°–70° C. the tetrahydrofuran was then removed from the mixture by distillation.

Dispersant 7

This was prepared in a similar manner to Dispersant 1, but using 95.7 g of Intermediate 2 and 7.36 g of "POLYMIN Waterfree".

Dispersant 8

This was prepared in a similar manner to Dispersant 1, but using 97.3 g of Intermediate 3 and 7.48 g of "POLYMIN Waterfree".

Dispersants 9 to 41

Table 1 lists a series of preparations carried out in the same manner as described for Dispersant 1, unless otherwise stated, using "POLYMIN Waterfree" as PEI. The other starting materials, the weights thereof, and reaction conditions are indicated in the table.

TABLE 1

| Dispersant No | Intermediate Number (Polyester) | Weight of Polyester (g) | Weight of PEI used (g) | Reaction time (hours) |
|---|---|---|---|---|
| 9 | 4 | 140 | 20 | 8 |
| 10 | 3 | 90 | 30 | 18 |
| 11 | 5 | 90 | 30 | 18 |
| 12 | 5 | 143 | 11 | 15 |
| 13 | 6 | 90 | 30 | 18 |
| 14 | 6 | 143 | 11 | 15 |
| 15 | 7 | 90 | 30 | 18 |
| 16 | 7 | 138 | 10.6 | 17 |
| 17 | 2 | 75 | 25 | 18 |
| 18 | 8 | 87.5 | 12.5 | 18 |
| 19 | 8 | 85 | 17 | 18 |
| 20 | 8 | 75 | 25 | 18 |
| 21 | 8 | 50 | 25 | 18 |
| 22 | 9 | 87.5 | 12.5 | 18 |
| 23 | 9 | 85 | 17 | 18 |
| 24 | 9 | 75 | 25 | 18 |
| 25 | 4 | 75 | 25 | 18 |
| 26 | 4 | 60 | 24 | 18 |
| 27 | 4 | 60 | 24 | 18 @ 120° C. & 5 @ 150° C. |
| 28 | 4 | 60 | 30 | 18 |
| 29 | 4 | 60 | 30 | 18 @ 120° C. & 5 @ 150° C. |
| 30 | 9 | 50 | 25 | 18 |
| 31 | 11 | 65 | 5 | 4 |
| 32 | 11 | 60 | 20 | 4.5 |
| 33 | 11 | 50 | 25 | 4.5 |
| 34 | 10 | 87.5 | 12.5 | 18 |
| 35 | 10 | 85 | 17 | 18 |
| 36 | 10 | 81 | 27 | 18 |
| 37 | 10 | 50 | 25 | 18 |
| 38 | 12 | 65 | 5 | 4 |
| 39 | 12 | 50 | 25 | 5 |
| 40 | 12 | 60 | 20 | 5 |
| 41 | 11 | 30 | 20 | 4.5 |

Dispersant 42

65 g of Dispersant 7 was stirred above its melting point (approximately 60° C.) and 4.05 g dimethyl sulphate added, causing the temperature to rise by approximately 15° C. The mixture was then stirred for 1½ hours at 85° C. to 95° C.

Dispersant 43

This was prepared in a similar manner to Dispersant 17, but using 68 g of Dispersant 8 and 4.05 g of dimethyl sulphate.

Dispersant 44

A mixture of 100 g of Intermediate 3 and 7.69 g of polyethyleneimine, having a number-average molecular wight of approximately 600, sold by the Dow Chemical Company under the name "MONTREK 6" (MONTREK is a trade mark), was stirred under nitrogen for 8 hours at 110° C. to 130° C. The product was a hard wax.

Dispersant 45

A mixture of 40 g of Intermediate 4 and 20 g of polyethyleneimine, having a number-average molecular weight of approximately 1800, sold by Dow Chemical Company under the name "MONTREK 18", was stirred under nitrogen for 5 hours at approximately 120° C.

Dispersant 46

A mixture of 10 g of "POLYMIN Waterfree", 100 g of E-caprolactone and 0.2 g of tetrabutyl titanate was stirred under nitrogen for 1 hour at 155°–160° C. and 45 minutes at 165°–170° C. The product, a hard wax, was shown by infra red spectroscopy to be free of unpolymerised E-caprolactone.

Comparative Dispersant 1 (CD 1)

A mixture of 150 g of poly-12-hydroxystearic acid having an acid value of 35 mg.KOH/g, and 50 g of "Polymin Waterfree" was stirred under nitrogen for 2 hours at 120° C. The mixture then had an acid value of approximately 18 mg.KOH/g. To the mixture was then added 200 g of iso-propanol to give the product, Comparative Dispersant 1, a solution having a solids content of approximately 50 wt %.

Coloured Acid 1 (CA 1)

This is copper phthalocyanine (CPC) sulphonic acid having, on average, 1.3 sulphonic acid groups per CPC nucleus.

Fluidising Agent 1 (FA 1)

To a stirred slurry of 300 g of a filter cake containing 85.6 g of copper phthalocyanine sulphonic acid (which contains, on average, 1.3 sulphuric acid groups per copper phthalocyanine nucleus) in 2L of water at 70°–75° C. is added 76 g of a commercially available mixture of 75% dioctadecyldimethyl ammonium chloride and 25% iso-propanol (ARQUAD 2HT-75; ARQUAD is a Registered Trade Mark). After stirring at 90°–100° C. for 2 hours the solid is filtered off, washed with water and dried.

Fluidising Agent 2 (FA 2)

Solution A: Tetra 3,3'-dichlorobenzidine was prepared by tetrazotising 38 g of 3,3'-dichlorobenzidine in 1200 g of water at 0° C.

Solution B: A mixture of 28 g acetoacetanilde (1st coupling component) and 46.5 g of potassium N-acetoacetyl-4-sulphanilate (2and coupling component) was stirred into 500 g of water. To the slurry were added 13.5 g of 46.7% sodium hydroxide, and the temperature raised to complete solution of the acetoacetanilide. To the solution were added 16 g of glacial acetic acid, 18.9 g of 36% hydrochloric acid and 700 g of water.

Coupling: Solution A was added to solution B over 75 minutes, the pH being controlled at 4.3 by the addition of sodium acetate. The reaction mixture was stirred overnight and then tested to ensure that no excess tetrazo was present.

The reaction mixture was then heated to 70° C., 75.5 g of dioctadecyldimethylammonium chloride (DODMAC) was added, and the mixture stirred for 1 hour at 70° C. The product, Fluidising Agent 2, made with equimolecular proportions of the two coupling components, was filtered off, washed with water and dried at 50°-60° C.

Fluidising Agent 3 (FA 3)

Solution A: Tetrazo-3,3'-dichlorobenzidine was prepared by tetrazotising 13.45 g of 3,3'-dichlorobenzidine in 500 g of water at 0° C.

Solution B: A mixture of 7.2 g of 2-naphthol and 12.3 g of the sodium salt of 6-hydroxy-2-naphthalene sulphonic acid (Schaeffer's acid) was stirred into 500 g of water. A 30% aqueous solution of sodium hydroxide was then added with stirring until the pH was 8.5.

Coupling: Solution A was added to Solution B over 1 hour, during which the temperature was maintained below 10° C. and pH was controlled at 8.5 by the addition of a 30% solution of sodium hydroxide. The reaction mixture was stirred for 1 hour, then heated to 90° C., cooled and filtered.

The filter cake was reslurried in 900 g of water, heated to 70° C. and the pH adjusted to 3 by the addition of dilute hydrochloric acid. To the stirred acid slurry was added 22.5 g of DODMAC over 10 minutes and the mixture stirred for 1 hour at 70° C. The product, Fluidising Agent 3, was filtered off, washed with water and dried at 50°-60° C.

EXAMPLES 1 to 75

The 75 dispersions, having the formulations described in Table 2, were prepared by ball milling the ingredients for 16 hours. All the resulting dispersions were fluid, deflocculated and with the pigment particles having a mean diameter below 5 microns.

TABLE 2

| Example | Pigment and Amount | Dispersant and Amount | Fluidising Agent/Coloured Acid & Amount | Org Liq and Amount |
|---|---|---|---|---|
| 1 | Yellow 34 7 g | Disp. 3 0.35 g | — | EOEA 2.65 g |
| 2 | Yellow 34 7 g | Disp. 1 0.35 g | — | EOEA 2.65 g |
| 3 | Yellow 34 7 g | Disp. 2 0.35 g | — | EOEA 2.65 g |
| 4 | Yellow 34 7 g | Disp. 4 0.35 g | — | EOEA 2.65 g |
| 5 | Yellow 34 7 g | Disp. 6 0.35 g | — | EOEA 2.65 g |
| 6 | Yellow 34 7.5 g | Disp. 5 0.375 g | — | EOEA 2.125 g |
| 7 | Yellow 34 7.5 g | Disp. 7 0.3 g | — | EOEA 2.2 g |
| 8 | Yellow 34 7.5 g | Disp. 8 0.3 g | — | EOEO 2.2 g |
| 9 | Yellow 34 7.5 g | Disp. 42 0.3 g | — | EOEA 2.2 g |
| 10 | Yellow 34 7.5 g | Disp. 43 0.3 g | — | EOEA 2.2 g |
| 11 | Yellow 34 8.0 g | Disp. 8 0.24 g | — | EOEA 1.76 g |
| 12 | White 6 8.0 g | Disp. 8 0.16 g | — | EOEA 1.84 g |
| 13 | Blue 15:2 3.0 g | Disp. 2 0.6 g | CA 1 0.3 g | EOEA 6.1 g |
| 14 | Blue 15:2 3.0 g | Disp. 5 0.6 g | CA 1 0.3 g | EOEA 6.1 g |
| 15 | Blue 15:2 3.0 g | Disp. 43 0.6 g | CA 1 0.3 g | EOEA 6.1 g |
| 16 | Blue 15:2 3.25 g | Disp. 8 0.65 g | CA 1 0.325 g | EOEA 5.775 g |
| 17 | Yellow 42 7.0 g | Disp. 2 0.28 g | — | EOEA 2.72 g |
| 18 | Yellow 42 7.0 g | Disp. 1 0.28 g | — | EOEA 2.72 g |
| 19 | Yellow 42 7.0 g | Disp. 2 0.28 g | — | EOEA 2.72 g |
| 20 | Yellow 42 7.0 g | Disp. 8 0.35 g | — | EOEA 2.65 g |
| 21 | Violet 19 3.0 g | Disp. 2 0.6 g | — | EOEA 6.4 g |
| 22 | Violet 19 3.0 g | Disp. 5 0.6 g | — | EOEA 6.4 g |
| 23 | Violet 19 3.5 g | Disp. 8 0.525 g | — | EOEA 5.975 g |
| 24 | Violet 19 3.5 g | Disp. 12 0.525 g | — | EOEA 5.975 g |
| 25 | Violet 19 3.5 g | Disp. 16 0.525 g | — | EOEA 5.975 g |
| 26 | Violet 19 3.75 g | Disp. 8 0.75 g | — | EOEA 5.5 g |
| 27 | Red 101 7.0 g | Disp. 2 0.28 g | — | EOEA 2.72 g |
| 28 | Red 101 7.0 g | Disp. 5 0.28 g | — | EOEA 2.72 g |
| 29 | Yellow 34 7.0 g | Disp. 1 0.28 g | — | MOPA 2.72 g |
| 30 | Yellow 34 7.0 g | Disp. 2 0.28 g | — | BA 2.72 g |
| 31 | Yellow 34 7.0 g | Disp. 3 0.28 g | — | BOEA 2.72 g |
| 32 | Yellow 34 7.0 g | Disp. 2 0.28 g | — | MEK 2.72 g |
| 33 | Yellow 34 7.0 g | Disp. 2 0.28 g | — | MIBK 2.72 g |
| 34 | White 6 7.5 g | Disp. 9 0.3 g | — | EOEA 2.2 g |
| 35 | Blue 15.3 3.0 g | Disp. 10 0.6 g | CA 1 0.3 g | ALC 6.1 g |
| 36 | White 6 7.0 g | Disp. 11 0.35 g | — | EOEA 2.65 g |
| 37 | White 6 7.0 g | Disp. 13 0.35 g | — | EOEA 2.65 g |
| 38 | Blue 15.3 3.0 g | Disp. 14 0.6 g | FA 1 0.3 g | EOEA 6.1 g |
| 39 | White 6 7.0 g | Disp. 15 0.35 g | — | EOEA 2.65 |
| 40 | Blue 15.3 3.0 g | Disp. 44 0.6 g | FA 1 0.3 g | EOEA 2.65 g |
| 41 | Blue 15.3 3.0 g | Disp. 17 0.6 g | CA 1 0.3 g | ALC 6.1 g |
| 42 | Red 57.1 3.0 g | Disp. 18 0.6 g | — | EA 6.4 g |
| 43 | Red 57.1 3.0 g | Disp. 19 0.6 g | — | EA 6.4 g |
| 44 | Blue 15.3 3.0 g | Disp. 20 0.6 g | CA 1 0.3 g | ALC 6.1 g |
| 45 | Blue 15.3 | Disp. 21 | CA 1 | ALC |

TABLE 2-continued

| Example | Pigment and Amount | Dispersant and Amount | Fluidising Agent/Coloured Acid & Amount | Org Liq and Amount |
|---|---|---|---|---|
| 46 | Red 57.1 3.0 g | Disp. 22 0.6 g | 0.3 g | 6.1 g EA 6.4 g |
| 47 | Red 57.1 3.0 g | Disp. 22 0.6 g | — | TOL 6.4 g |
| 48 | Red 57.1 3.0 g | Disp. 23 0.6 g | — | EA 6.4 g |
| 49 | Blue 15.3 3.0 g | Disp. 24 0.6 g | CA 1 0.3 g | ALC 6.1 g |
| 50 | Blue 15.3 3.0 g | Disp. 25 0.6 g | CA 1 0.3 g | ALC 6.1 g |
| 51 | Blue 15.3 3.0 g | Disp. 26 0.6 g | CA 1 0.3 g | ALC 6.1 g |
| 52 | Blue 15.3 3.0 g | Disp. 27 0.6 g | CA 1 0.3 g | ALC 6.1 g |
| 53 | Blue 15.3 3.0 g | Disp. 28 0.4 g | CA 1 0.2 g | ALC 6.4 g |
| 54 | Blue 15.3 3.0 g | Disp. 28 0.6 g | CA 1 0.3 g | ALC 6.1 g |
| 55 | Blue 15.3 3.0 g | Disp. 29 0.6 g | CA 1 0.3 g | ALC 6.1 g |
| 56 | Blue 15.3 3.0 g | Disp. 30 0.6 g | CA 1 0.3 g | ALC 6.1 g |
| 57 | White 6 7.0 g | Disp. 31 0.35 g | — | XYL 2.65 g |
| 58 | White 6 7.0 g | Disp. 32 0.35 g | — | XYL 2.65 g |
| 59 | Blue 15.3 3.0 g | Disp. 32 0.6 g | CA 1 0.3 g | ALC 6.1 g |
| 60 | Blue 15.3 3.0 g | Disp. 33 0.6 g | CA 1 0.3 g | ALC 6.1 g |
| 61 | Red 57.1 3.0 g | Disp. 34 0.6 g | — | EA 6.4 g |
| 62 | Red 57.1 3.0 g | Disp. 35 0.6 g | — | EA 6.4 g |
| 63 | Blue 15.3 3.0 g | Disp. 36 0.6 g | CA 1 0.3 g | ALC 6.1 g |
| 64 | Blue 15.3 3.0 g | Disp. 37 0.6 g | CA 1 0.3 g | ALC 6.1 g |
| 65 | White 6 7.0 g | Disp. 38 0.35 g | — | XYL 2.65 g |
| 66 | Blue 15.3 3.0 g | Disp. 39 0.6 g | CA 1 0.3 g | ALC 6.1 g |
| 67 | Blue 15.3 3.0 g | Disp. 40 0.6 g | CA 1 0.3 g | ALC 6.1 g |
| 68 | Yellow 12 3.0 g | Disp. 8 0.6 g | FA 2 0.3 g | EA 6.1 g |
| 69 | Blue 15.3 3.0 g | Disp. 10 0.6 g | CA 1 0.3 g | ALC/EA 50/50 6.1 g |
| 70 | Red 4 3.0 g | Disp. 9 0.6 g | FA 3 0.3 g | EA 6.1 g |
| 71 | Red 214 3.0 g | Disp. 8 0.6 g | FA 3 0.3 g | EA 6.1 g |
| 72 | Blue 15.3 3.0 g | Disp. 41 0.6 g | CA 1 0.3 g | ALC 6.1 g |
| 73 | Blue 15.3 3.0 g | Disp. 45 0.6 g | CA 1 0.3 g | ALC 6.1 g |
| 74 | Blue 15.3 3.0 g | Disp. 46 0.6 g | FA 1 0.3 g | MIBK 6.1 g |
| 75 | White 6 7.0 g | Disp. 46 0.35 g | — | MIBK 2.65 g |

EXAMPLES 76 to 82

The dispersions, having the formulations described in Table 3, were prepared by ball-milling the ingredients in a high-energy ball mill with 3 mm glass beads for 30 minutes. All the resulting dispersions were fluid, deflocculated and with pigment particles having a mean diameter below 5 microns.

TABLE 3

| Example | Pigment and Amount | Dispersant and Amount | Fluidising Agent/Coloured Acid & Amount | Org Liq and Amount |
|---|---|---|---|---|
| 76 | Green 7 16.41 g | Disp. 8 2.46 g | — | MOPA 28.02 g |
| 77 | Green 36 17.07 g | Disp. 8 2.56 g | — | MOPA 29.14 g |
| 78 | Red 122 9.34 g | Disp. 8 1.87 g | — | MIAK 26.17 g |
| 79 | Blue 60 11.89 g | Disp. 8 2.38 g | — | MIAK 25.37 g |
| 80 | Yellow 173 9.55 g | Disp. 8 1.91 g | — | MIAK 26.75 g |
| 81 | Blue 15:2 17.8 g | Disp. 8 1.42 g | FA 1 0.71 g | MOPA 24.75 g |
| 82 | Yellow 155 14.58 g | Disp. 8 2.18 g | — | MOPA 25.79 g |

The following abbreviations are used in Tables 2 & 3:
EOEA is 2-ethoxyethyl acetate
BA is butyl acetate
MOPA is 3-methoxypropyl acetate
ALC is Ethanol
BOEA is 2-butoxyethyl acetate
EA is Ethyl acetate
MEK is methylethyl ketone
TOL is Toluene
MIBK is methyliso-butyl ketone
XYL is Xylene
MIAK is methyliso-amyl ketone
CA 1 is Coloured Acid 1
FA 1 is Fluidising Agent 1
FA 2 is Fluidising Agent 2
FA 3 is Fluidising Agent 3

COMPARATIVE EXAMPLE 1

A mixture of 7.0 g of Pigment Yellow 34, 0.7 g of Comparative Dispersant 1 and 2.3 g of EOEA was ball-milled for 16 hours under the same conditions as Examples 1 to 75. The mixture became thick and the pigment failed to disperse satisfactorily.

To evaluate the use of the dispersions in accordance with the present invention in high solids paint systems, the paints described below in Examples 83 to 91 were prepared.

EXAMPLES 83 to 87

The high solids paint system employed in Examples 83 to 87 was an oil-free polyester combined with a hexamethoxymethyl melamine resin in the presence of a catalyst, p-toluene sulphonic acid. The oil-free polyester had an acid value of 10 mg.KOH/g maximum, a hydroxy value of 110–130 mg.KOH/g and is available from Croda Resins Ltd, in the form of an 80% solution in EOEA, as PLASTOKYD HS-900 (PLASTOKYD is a registered trade mark). The hexamethoxymethyl melamine resin was from British Industrial Plastics Ltd in 100% active form, as BEETLE RESIN 3745 (BEETLE is a registered trade mark). In some paint formulations a levelling agent or resin modifier was also added.

Mill-bases were prepared in a ball-mill, and in each case the mean particle diameter of the pigment after milling, was below 5 microns. After milling, the mill-base was converted into a usable paint by the addition of a let-down lacquer. Details of the mill-bases and let-down lacquers are shown in Table 4 in which all quantities are in grams.

TABLE 4

| | Example 83 | Example 84 | Example 85 | Example 86 | Example 87 |
|---|---|---|---|---|---|
| Mill-bases | | | | | |
| Pigment Yellow 34 | 27.0 | | | | |

TABLE 4-continued

|  | Example 83 | Example 84 | Example 85 | Example 86 | Example 87 |
|---|---|---|---|---|---|
| Pigment White 6 |  | 39.3 |  |  |  |
| Pigment Blue 15:2 |  |  | 12.0 |  |  |
| Pigment Yellow 42 |  |  |  | 28.8 |  |
| Pigment Violet 19 |  |  |  |  | 12.0 |
| Dispersant 8 | 1.35 | 0.79 | 1.56 | 1.15 | 1.8 |
| EOEA | 8.25 | 8.12 | 22.58 | 10.61 | 20.48 |
| MODAFLOW | 0.6 | 0.92 |  |  |  |
| RESIFLOW FL2 |  |  |  | 0.54 |  |
| Coloured Acid 1 |  |  | 0.78 |  |  |
| Let-down Lacquers |  |  |  |  |  |
| PLASTOKYD HS-900 | 49.9 | 41.9 | 116.2 | 99.8 | 116.2 |
| BEETLE Resin 3745 | 13.3 | 11.17 | 31.0 | 26.6 | 31.0 |
| p-Toluene sulphonic acid | 0.5 | 0.5 | 1.0 | 1.0 | 1.0 |
| EOEA | 2.0 | 3.14 | 29.68 | 23.02 | 25.92 |
| MODAFLOW |  | 0.28 |  |  |  |
| RESIFLOW FL2 |  |  |  | 0.66 |  |
| PA 57 |  |  | 1.6 |  |  |

In Table 4, MODAFLOW, RESIFLOW FL2 and PA 57 are levelling agents or resin modifiers for paints, available from Monsanto Industrial Chemicals, Worlee-Chemie GmbH and Dow Corning Europe respectively (MODAFLOW and RESIFLOW are registered trademarks).

Test panels on anodised aluminium were prepared for each of the above paints. Paints were applied with a 250 μm well applicator and a wire-wound K-bar (Meyer bar). Gloss, hardness, adhesion and moisture resistance were all satisfactory.

EXAMPLE 88

A high solids paint system were prepared incorporating an aliphatic polyisocyanate cross-linked with a hydroxyl functional acrylic resin, which also contained an oxazolidine functional modifier to increase paint solids.

The aliphatic polyisocyanate used had an -NCO content of 23.5% and is available from Bayer AG in a 100% form as DESMODUR L2291 (DESMODUR is a Registered Trade Mark). The hydroxyl functional acrylic crosslinker used had an equivalent weight of 425 and is available from Rohm and Haas Company in the form of a 67% solution in methyl-n-amyl ketone as Experimental Resin QR-946. The oxazolidine functional modifier used had an equivalent weight of 100 and is also available from Rohm and Haas Company in a 97–99.5% form as Experimental Reactive Modifier QM-1007.

A mill-base was prepared in a ball-mill, and the mean particle diameter of the pigment after milling was below 5 microns. After milling, the mill-base was converted into a usable paint by the addition of let-down lacquers. Let-down was carried out in two stages. The product of the first let-down stage is stable almost indefinitely, whilst the second stage let-down gave a usable paint which had a pot-life of a only few hours. Details of the millbase and let-down lacquers are shown in Table 5.

TABLE 5

|  | Weight (g) |
|---|---|
| Millbase |  |
| Experimental Resin QR-946 | 18.4 |
| Pigment White 6 | 3.37 |
| Pigment Blue 15.2 | 11.25 |
| Methyl-n-amyl ketone | 10.62 |
| Dispersant 8 | 0.90 |
| Fluidising Agent 1 | 0.45 |

TABLE 5-continued

|  | Weight (g) |
|---|---|
| First Stage Let-down Lacquer |  |
| Experimental Resin QR-946 | 41.0 |
| Experimental reactive modifier QM-1007 | 26.6 |
| Methyl-n-amyl ketone | 14.0 |
| MODAFLOW | 0.08 |
| Second Stage Let-down Lacquer |  |
| DESMODUR L-2291 | 67.8 |
| Methyl-n-amyl ketone | 5.0 |

Test panels on anodised aluminium were prepared by applying the above paint with a wire-wound K-bar (Meyer Bay). Gloss, hardness, adhesion and moisture resistance were all satisfactory.

EXAMPLE 89

A high solids stoving (baking) paint system was prepared incorporating a short-oil alkyd resin combined with a hexamethoxymethylmelamine resin in the presence of a catalyst, p-toluene sulphonic acid. The short-oil alkyd resin was of the tall oil fatty acid type, 90% solids by weight in EOEA, and is available from Cargill Inc., U.S.A. under the product code 5710. The hexamethoxymethylmelamine resin was essentially 100% solids, had a viscosity in the range Y-Z3 on the Gardner Holdt scale, and is also available from Cargill Inc. under the product code 2347.

The millbase was prepared in a ball mill, and the mean particle diameter of the pigment after milling was below 5 microns. After milling, the mill-base was converted into a usable paint by the addition of let-down lacquer. Details of the mill-base and let-down lacquer are shown in Table 6.

TABLE 6

|  | Weight (g) |
|---|---|
| Millbase |  |
| Pigment White 6 | 69.30 |
| Dispersant 8 | 0.83 |
| MOPA | 19.87 |
| Let-down Lacquer |  |
| CARGILL 5710 | 77.00 |
| CARGILL 2347 | 17.33 |
| BYK 300 | 0.30 |
| p-Toluene sulphonic acid (20% solution in MOPA) | 2.00 |
| MOPA | 4.53 |

BYK 300 is a levelling agent available from Byk-Chemie, U.S.A. (BYK is a Registered Trade Mark).

Test panels on tinplate and anodised aluminium were prepared by applying the above paint with a wire-wound K-bar. Gloss, adhesion and moixture resistance were all satisfactory.

EXAMPLES 90 and 91

High solids air-drying paint systems were prepared incorporating Soya oil alkyd resins. The resins used were Cargill products 5713 (an 80% solids solution in butyl acetate, with viscosity: Z4-Z6 and acid number: 10) and 5725 (an 80% solids solution in EOA, with viscosity: Z4-Z5 and acid number: 6).

Millbases were prepared in a ball mill, and the mean particle diameter of the pigment after milling was below 5 microns. After milling the millbases were converted into usable paints by the addition of let-down lacquer. Details of the mill-base and let-down lacquers are shown in Table 7.

TABLE 7

|  | Example 90 Weight (g) | Example 91 Weight (g) |
|---|---|---|
| Mill-bases | | |
| Pigment White 6 | 69.30 | 69.30 |
| Dispersant 8 | 0.83 | 0.83 |
| MIAK | 19.87 | 19.87 |
| Let-down Lacquer | | |
| Cargill Resin 5713 | 108.28 | |
| Cargill Resin 5725 | | 108.28 |
| MIAK | 14.28 | |
| 1,1,1-Trichloroethane | | 14.28 |
| Mixed Drier: (mixture of Co, Pb & Ca naphthenates) | 4.00 | 4.00 |

Test panels on tinplate and anodised aluminium were prepared by applying the above paints with a wire-wound K-bar. Gloss and adhesion were both satisfactory.

To evaluate the use of a dispersion in accordance with present invention in a conventional paint system, the paint described in Example 92 below was prepared.

EXAMPLE 92

A stoving (baking) paint system was prepared incorporating a non-drying alkyd resin combined with a melamine-formaldehyde resin. The alkyd resin used was glycerol-based, acid value 7mg.KOH/g and is supplied as a 70% solution in xylene by Croda Resins Ltd., under the name PLASTOKYD C-30AX (PLASTOKYD is a Registered Trade Mark). The melamine-formaldehyde resin used was of the n-butylated type, and is supplied as a 60% solution in n-butanol by British Industrial Plastics Ltd., under the name BEETLE BE 615 (BEETLE is a Registered Trade Mark).

The mill-base was prepared in a ball mill, and the mean particle diameter of the pigment after milling was below 5 microns. After milling the mill-base was converted into a usable paint by the addition of let-down lacquers in two stages. Details of the mill-base and the let-down lacquers are shown in Table 8.

TABLE 8

|  | Weight (g) |
|---|---|
| Millbase | |
| Pigment Blue 60 | 11.70 |
| Dispersant 8 | 1.40 |
| Xylene | 20.48 |
| n-Butanol | 5.12 |
| Fluidising Agent 1 | 0.35 |
| First Stage Let-down Lacquer | |
| PLASTOKYD C-30AX | 18.92 |
| Xylene | 15.95 |
| n-Butanol | 3.99 |
| Second Stage Let-down Lacquer | |
| PLASTOKYD C-30AX | 97.60 |
| BEETLE BE 615 | 58.50 |

Test panels on tinplate and anodised aluminium were prepared by applying the above paints using a wire-wound K-bar or an air-driven spray gun as appropriate. Gloss, adhesion and scratch resistance were all satisfactory.

EXAMPLES 93 to 97

The formulations described in Table 9 below are similar to those used in different types of ceramic tape casting or doctor blade processes. In Examples 93 and 94 typical resin binders and plasticisers are also included in the dispersion formulation. In Examples 95 to 97 only dispersant, solvent(s) and ceramic powder are included in the dispersion formulation.

In Examples 93 to 95, the dispersions were prepared by ball milling the ingredients in a high-energy ball mill with 3 mm glass balls for 30 minutes. In Examples 96 and 97 the dispersions were prepared by ball milling the ingredients for 16 hours. All the resulting dispersions were fluid and deflocculated.

TABLE 9

| Ingredients | Example 93 | Example 94 | Example 95 | Example 96 | Example 97 |
|---|---|---|---|---|---|
|  | (weight in g) | | | | |
| A-16 Alumina | 50.32 | 47.02 | 62.40 | | |
| Barium Titanate | | | | 12.23 | |
| Zirconium Oxide | | | | | 8.96 |
| Dispersant 8 | 1.70 | | 2.18 | 0.25 | 0.27 |
| Dispersant 9 | | 1.64 | | | |
| Trichloroethylene | 19.62 | 18.34 | | 1.53 | 3.08 |
| Ethanol | 7.55 | 7.05 | 8.62 | 0.59 | |
| Methylethylketone | | | 8.62 | | |
| Polyvinyl butyral | | 1.88 | | | |
| PEG 2000 | 2.16 | 2.02 | | | |
| Dioctyl phthalate | 1.81 | 1.69 | | | |

A-16 Alumina is a calcined alumina, ultimate crystal size 0.3–0.5 μm, supplied by the Aluminium Company of America.

The barium titanate is "Grade S" supplied by Anzon Ltd., of Newcastle, England. It has an average particle size of 1.49 μm, and it is of the type typically used in ceramic capacitors.

The zirconium oxide id "Grade SC15" supplied by Magnesium Elektron Ltd., of England. It has an average particle size of less than 2 μm.

PEG 2000 is polyethylene glycol, with a molecular weight of about 2000.

The polyvinyl butyral was supplied by the Aldrich Chemical Co., and had a molecular weight of about 36000.

We claim:

1. A composition comprising a finely-divided non-magnetic solid dispersed in an organic medium selected from amines, ether, organic acids, esters, ketones, glycols, glycol ethers, glycol esters, amides, aromatic hydrocarbons, halogenated aromatic and aliphatic hydrocarbons and polar, film-forming resins in the presence of a dispersant comprising a poly($C_{2-4}$-alkyleneimine) carrying at least two mono- or poly-(carbonyl-$C_{1-7}$-alkyleneoxy) groups.

2. A composition according to claim 1 wherein the solid is selected from pigments, extenders, fillers, disperse dyes, optical brightening agents, textile auxiliaries, oil-based and invertemulsion drilling mud solids, dirt and soil particles, particulate ceramic materials, biocides, agrochemicals and pharmaceuticals.

3. A composition according to claim 1 or claim 2 wherein the solid is dispersed in an organic medium.

4. A composition according to claim 1 or claim 2 wherein the organic medium is a polar organic medium selected from glycol ethers, glycol esters, dialkyl- and cycloalkyl-ketones, alkyl esters of alkanecarboxylic acids, dialkyl and cycloalkyl-ethers containing up to 6 carbon atoms, polyester and polyamide resins and cellulose ethers.

5. A composition according to claim 1 or claim 2 wherein the dispersant is a compound of the formula:

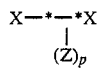

wherein

X—*—*X represents a poly (C$_{2-4}$-alkyleneimine) (PAI)

Z represents a mono(carbonylalkyleneoxy) (CAO) group or a poly(carbonyl-C$_{1-7}$-alkyleneoxy) (PCAO) group linked to the PAI through an amide or salt link;

and p is a number from to 2000.

6. A composition according to claim 5 wherein the CAO and PCAO groups are of the formula:

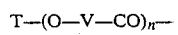

wherein

T is H or a terminal chain stopping group;

V is a C$_{1-7}$-alkylene group;

and n is a number from 1 to 100.

7. A composition according to claim 5 in which p is 4 to 2000.

8. A composition of a finely-divided non-magnetic solid and a dispersant of the formula:

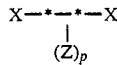

wherein

X—*—*—X represents a poly (C$_{2-4}$-alkyleneimine);

Z represents a mono(carbonylalkyleneoxy) group or a poly(carbonylalkyleneoxy) group linked to the poly(C$_{2-4}$-alkyleneimine) through an amide or salt link;

and p is a number from 4 to 2000.

9. A composition comprising a finely-divided non-magnetic solid dispersed in an organic medium selected from the group consisting of amines, ethers, organic acids, esters, ketones, glycols, glycol ethers, glycol esters, amides, aromatic hydrocarbons, halogenated aromatic and aliphatic hydrocarbons and polar, film-forming resins, in the presence of a dispersant comprising a poly(C$_{2-4}$-alkyleneimine) carrying from 2 to 2000 poly(carbonyl-C$_{3-6}$-alkyleneoxy) groups.

10. A composition according to claim 6 in which V is pentamethylene.

11. A composition according to claim 5 wherein Z represents carbonylpentamethyleneoxy or a poly(carbonylpentamethyleneoxy) group linked to the PAI through an amide or salt link.

* * * * *

UNITED STATES PATENT AND TRADEMARK OFFICE
CERTIFICATE OF CORRECTION

PATENT NO. : 4,861,380

DATED : August 29, 1989

INVENTOR(S) : CAMPBELL et al.

It is certified that error appears in the above-identified patent and that said Letters Patent is hereby corrected as shown below:

On the title page

Please correct filing date:

From - October 22, 1988
    to
    --October 27, 1988--

Signed and Sealed this

Ninth Day of October, 1990

Attest:

HARRY F. MANBECK, JR.

*Attesting Officer*  *Commissioner of Patents and Trademarks*